(12) United States Patent
Leblanc et al.

(10) Patent No.: US 11,554,093 B2
(45) Date of Patent: Jan. 17, 2023

(54) ACRYLIC HAIR FIXATIVE COPOLYMERS AND COMPOSITIONS

(71) Applicant: NOURYON CHEMICALS INTERNATIONAL B.V., Arnhem (NL)

(72) Inventors: Jean-Pierre Leblanc, Hillsborough, NJ (US); Michael Timothy Philbin, Hopewell, NJ (US)

(73) Assignee: NOURYON CHEMICALS INTERNATIONAL B.V., Arnhem (NL)

( * ) Notice: Subject to any disclaimer, the term of this patent is extended or adjusted under 35 U.S.C. 154(b) by 0 days.

(21) Appl. No.: 15/560,368

(22) PCT Filed: Apr. 20, 2016

(86) PCT No.: PCT/EP2016/058712
§ 371 (c)(1),
(2) Date: Sep. 21, 2017

(87) PCT Pub. No.: WO2016/169957
PCT Pub. Date: Oct. 27, 2016

(65) Prior Publication Data
US 2018/0098930 A1  Apr. 12, 2018

Related U.S. Application Data

(60) Provisional application No. 62/149,955, filed on Apr. 20, 2015.

(30) Foreign Application Priority Data

May 29, 2015  (EP) .................................... 15169961

(51) Int. Cl.
| | | |
|---|---|---|
| *A61K 9/00* | (2006.01) | |
| *A61K 8/81* | (2006.01) | |
| *A61Q 5/06* | (2006.01) | |
| *C08F 220/18* | (2006.01) | |
| *A61K 8/04* | (2006.01) | |

(52) U.S. Cl.
CPC ............ *A61K 8/8158* (2013.01); *A61K 8/046* (2013.01); *A61K 8/8147* (2013.01); *A61K 8/8152* (2013.01); *A61Q 5/06* (2013.01); *C08F 220/1811* (2020.02)

(58) Field of Classification Search
CPC .................................................... A61K 8/8158
See application file for complete search history.

(56) References Cited

U.S. PATENT DOCUMENTS

| | | |
|---|---|---|
| 3,927,199 A | 12/1975 | Micchelli et al. |
| 4,192,861 A | 3/1980 | Micchelli et al. |
| 4,315,910 A | 2/1982 | Nowak, Jr. et al. |
| 5,576,403 A | 11/1996 | Chandran et al. |
| 5,632,976 A | 5/1997 | Chandran et al. |
| 5,686,062 A | 11/1997 | Tong |
| 5,886,101 A | 3/1999 | Sommerfeld et al. |
| 6,482,393 B1 | 11/2002 | Schehlmann et al. |
| 6,734,244 B2 | 5/2004 | Confalone et al. |
| 7,329,705 B2 | 2/2008 | Farwaha et al. |
| 8,815,223 B2 | 8/2014 | Collin et al. |
| 9,233,064 B2 | 1/2016 | Jordan et al. |
| 9,302,126 B2 | 4/2016 | Gao et al. |
| 9,345,656 B2 | 5/2016 | Weber et al. |
| 10,300,005 B2 | 5/2019 | Wang et al. |
| 2007/0141013 A1 | 6/2007 | Nguyen-Kim et al. |
| 2010/0316586 A1 | 12/2010 | Knappe et al. |
| 2014/0255478 A1* | 9/2014 | Martino ................... A61Q 5/06 424/451 |

FOREIGN PATENT DOCUMENTS

| | | |
|---|---|---|
| CA | 981183 A | 1/1976 |
| EP | 0 364 887 A2 | 4/1990 |
| JP | S 49-14647 A | 2/1974 |
| JP | H 10-182370 A | 7/1998 |
| KR | 2012/118215 A | 10/2012 |
| WO | 2006/128608 A1 | 12/2006 |

OTHER PUBLICATIONS

International Search Report and Written Opinion for PCT/EP2016/058712 dated Aug. 22, 2016.
European Search Report filed in 15169961.8-1460 dated Nov. 20, 2015.
International Preliminary Report on Patentability for PCT/EP2016/058712 dated Mar. 16, 2017.

\* cited by examiner

*Primary Examiner* — Paul W Dickinson
(74) *Attorney, Agent, or Firm* — Norris McLaughlin, P.A.

(57) ABSTRACT

A hair fixative composition comprising a film forming polymer that is prepared from monomers comprising (a) 10-30% by weight of one or more copolymerizable comonomers selected from the group consisting of N-alkyl (meth)acrylamide wherein the alkyl group thereof contains from 2 to 12 carbon atoms, wherein for at least one of said copolymerizable comonomers the alkyl group contains from 5 to 12 carbon atoms; (b) 14-21% by weight of copolymerizable comonomers comprising acrylic acid and optionally one or more acidic copolymerizable comonomers selected from the group consisting of methacrylic acid, crotonic acid, itaconic acid, maleic acid, fumaric acid, and the ($C_1$-$C_4$)alkyl half esters of maleic and fumaric acids; and (c) 40-76% by weight two or more copolymerizable comonomers selected from the group consisting of ($C_1$-$C_{12}$)alkyl(meth)acrylates, wherein at least one of said two or more copolymerizable comonomers is a ($C_1$-$C_2$)alkyl(meth)acrylate; said film forming polymer being optionally completely or partially neutralized with a basic reagent.

6 Claims, No Drawings

ACRYLIC HAIR FIXATIVE COPOLYMERS AND COMPOSITIONS

This application is a national stage filing under 35 U.S.C. § 371 of PCT/EP2016/058712, filed Apr. 20, 2016, which claims priority to U.S. Provisional Patent Application No. 62/149,955 filed Apr. 20, 2015, and European Patent Application No. 15169961.8, filed May 29, 2015, the contents of which are each incorporated herein by reference in their entireties.

FIELD OF THE INVENTION

This invention relates to film forming polymers and to hair fixing compositions containing the unique film forming polymers described herein.

BACKGROUND OF THE INVENTION

In order to be highly effective in hair fixing compositions such as aerosol hair sprays and hair setting lotions, the film forming polymers utilized therein as well as the films derived therefrom must meet a rigid set of requirements. Thus, the polymers used in such formulations should be soluble in anhydrous organic solvents, yet the films cast from such hair fixing formulations should, ordinarily, either be water soluble or water dispersible in order to facilitate their easy removal from the user's hair. As is readily visualized, this is an unusual combination of properties which is further complicated by the requirement that the polymers used in such formulations be completely compatible with the solvents and/or propellants ordinarily employed therein. Furthermore, the polymers used should show little or no tendency to interact with the perfumes or other optional ingredients utilized in hair fixing formulations.

In addition, the films cast from either aqueous or organic solvent solutions of these polymers should be flexible and should simultaneously exhibit sufficient strength and elasticity; they should exhibit good adhesion to hair so as to avoid the occurrence of dusting or flaking when the hair is subjected to varying stresses; they should readily allow the hair to be recombed; they should maintain a non-tacky state despite humid conditions; they should be clear, transparent and glossy and should possess good antistatic properties; and they should be easily removable by the use of water and/or soap or shampoo.

It is also desirable that a hair fixative product should be able to provide excellent hold, even in high humidity conditions, while still providing a feel that is more natural and is not too hard, and while allowing for flexibility of the hair. Such a hair fixative product would desirably have good stiffness, spring and webbing.

Many polymeric systems have been utilized in an attempt to meet these stringent requirements. Among these are included: polyvinylpyrrolidone, copolymers of N-vinyl pyrrolidone with vinyl acetate, 5-5'-dimethyl hydantoinformaldehyde resins, and copolymers of methyl vinyl ethers and maleic acid half esters, etc.

Acrylate resins containing acrylic monomers copolymerized with other monomers also have been used in hair fixative compositions.

U.S. Pat. No. 6,482,393 discloses hairsetting compositions comprising 30-72% by weight of tert-butyl (meth) acrylate, 10-28% by weight of acrylic acid or methacrylic acid or a mixture thereof, and 0-60% by weight of a copolymerizable monomer the homopolymer of which having a glass transition temperature of less than 30° C.

US 2007/0141013 A1 discloses amphoteric copolymers containing a molar excess of anionogenic and/or anionic groups, polyelectrolyte complexes containing the ampholytic copolymer, and compositions containing the copolymer or polyelectrolyte complex.

EP 0 364 887 A2 discloses a hair fixing composition comprising a polymer made by copolymerizing about 0-60% by weight of a $C_3$-$C_{12}$ alkyl acrylate or methacrylate, about 15-75% by weight $C_4$-$C_{10}$ N-substituted acrylamide, and about 20-35% by weight acrylic acid or methacrylic acid.

Other polymers and compositions are disclosed, for example, in U.S. Pat. Nos. 3,927,199; 4,315,910; and 5,686,062; each of which is incorporated herein by reference in its entirety. Certain such prior art film forming polymers are acrylates/octylacrylamide copolymers. Other such prior art film forming polymers are octylacrylamide/acrylates/butylaminoethyl methacrylate copolymers. Both types of copolymers are well known in the hair fixative industry, and provide excellent performance properties such as high humidity curl retention.

Some consumers, however, prefer a fixative composition having good high humidity curl retention but also having a feel that is less stiff and more natural, and allowing for more flexibility in styling.

In addition, some of the monomers used in acrylates/octylacrylamide copolymers and octylacrylamide/acrylates/butylaminoethyl methacrylate copolymers can be costly. In particular, (meth)acrylamide monomers, hydroxylalkyl (meth)acrylate monomers, and alkyl amino alkyl methacrylate monomers are all relatively expensive. It would be desirable to provide acrylic copolymers having properties as least as good as the properties of existing film forming polymers but using less of the more expensive monomers, or even eliminating some of the more expensive monomers altogether.

It is an object of this invention to provide film forming polymers suitable for use in hair fixing formulations, said polymers exhibiting most or all of the above-described properties.

It is a further object to provide hair fixing compositions using the film forming polymers of the present invention.

It is a further object of the invention to provide such film forming polymers which are also compatible with different propellant systems, including non-polar hydrocarbon propellants, polar propellants, and hydrofluorocarbon propellants.

Various other objects and advantages of this invention will become apparent from a reading of the disclosure which follows hereinafter.

SUMMARY OF THE INVENTION

We have now discovered that all of the previously described requirements for an effective hair fixing formulation are met by utilizing the novel class of polymers hereinafter described as the film forming polymer component of the hair fixing compositions of this invention. Thus the present invention relates to film forming copolymers prepared from monomers comprising one or more selected copolymerizable N-alkyl (meth)acrylamide monomers, one or more selected copolymerizable acidic monomers, and two or more copolymerizable monomers selected from the group as hereinafter defined. The invention further relates to hair fixative compositions comprising such film forming polymers.

DETAILED DESCRIPTION OF THE INVENTION

The terminology "(meth)acrylate" and "(meth)acrylamide" as used herein shall be intended as encompassing both methacrylate and acrylate, and both methacrylamide and acrylamide, respectively, unless expressly stated otherwise.

Acrylic polymer, as used herein, is intended to include those polymers which contain at least one α-β ethylenically unsaturated acidic monomer containing one or more carboxylic groups. Preferred acrylic, film forming polymers utilized in the hair fixative compositions of this invention comprise polymers containing the residues of at least one monomer which is an N-alkyl (meth)acrylamide, at least one acidic monomer containing one or more carboxyl groups, and at least two monomers selected from a group of monomers which are copolymerizable with the acidic monomers, hereinafter referred to as a copolymerizable monomers.

All percentages stated in this application are weight percentages unless stated otherwise.

In accordance with the invention, a hair fixative composition comprises a film forming copolymer that is prepared from monomers comprising
  (a) 10-30% of one or more copolymerizable comonomers selected from the group consisting of N-alkyl (meth) acrylamide wherein the alkyl group thereof contains from 2 to 12 carbon atoms, wherein for at least one of said copolymerizable comonomers the alkyl group contains from 5 to 12 carbon atoms;
  (b) 14-21% of one or more acidic copolymerizable comonomers selected from the group of acrylic acid and optionally one or more from the group of methacrylic acid, crotonic acid, itaconic acid, maleic acid, fumaric acid, and the ($C_1$-$C_4$)alkyl half esters of maleic and fumaric acids; and styrenesulfonic acid or their salts; and
  (c) two or more copolymerizable comonomers selected from the group consisting of ($C_1$-$C_{12}$)alkyl(meth)acrylates, wherein at least one of said two or more copolymerizable comonomers is a ($C_1$-$C_2$)alkyl(meth)acrylate; said film forming polymer being optionally neutralized with an alkaline reagent.

The invention also encompasses hair fixative compositions comprising the hair fixative copolymers of the invention. Particularly significant are the broadened solubility and compatibility characteristics exhibited by the polymers in the hair fixative compositions of the present invention. Thus, for example, they display a greater degree of solubility in the organic solvents typically used in aerosol hair sprays as well as in the aqueous solvent systems typically utilized in wave set lotions. In addition, they exhibit greater compatibility with the hydrocarbon propellants typically used in aerosol hair sprays The Comonomers
  Component (a)
  The applicable N-alkyl(meth)acrylamides of component (a) include at least one comonomer wherein the alkyl radical contains from 5-12 carbon atoms. Among the applicable acrylamides and methacrylamides are included without limitation N-n-octyl acrylamide, N-tertiary-octyl acrylamide, N-decyl acrylamide, N-dodecyl acrylamide, as well as the corresponding N-substituted methacrylamides. In one embodiment component (a) comprises N-tertiary-octyl acrylamide.

In addition to the ($C_5$-$C_{12}$)alkyl(meth)acrylamides, ($C_2$-$C_4$)alkyl(meth)acrylamides such as N-ethyl acrylamide and N-tertiary-butyl acrylamide also may be present.

In one embodiment, component (a) comprises at least some comonomer wherein the alkyl radical contains from 5 to 12 carbon atoms; in one embodiment component (a) comprises at least 50% by weight of comonomers wherein the alkyl radical contains from 5 to 12 carbon atoms; in one embodiment, component (a) comprises at least 75% by weight of comonomers wherein the alkyl radical contains from 5 to 12 carbon atoms; in one embodiment, component (a) comprises 100% comonomers wherein the alkyl radical contains from 5 to 12 carbon atoms. In one embodiment, comonomer (a) is 100% N-tertiary-octyl acrylamide.

Component (b)
Component (b) comprises monomers which contain at least one available carboxylic acid group. In one embodiment, component (b) comprises acrylic acid, and optionally comprises one or more additional copolymerizable acidic comonomers selected from methacrylic acid, crotonic acid, itaconic acid, maleic acid, fumaric acid and the ($C_1$-$C_4$) alkyl half esters of maleic and fumaric acids such as methyl hydrogen maleate and butyl hydrogen fumarate, styrenesulfonic acid or their salts, as well as any other acidic monomers which are capable of being copolymerized with the particular polymer system whose use is desired by the practitioner. As is known to those skilled in the art, the acidic monomers must be so chosen as to be readily polymerizable with the selected polymer system.

In one embodiment the acidic comonomer of component (b) comprises acrylic acid, in one embodiment component (b) comprises a mixture of acrylic acid and methacrylic acid. In one embodiment in which component (b) comprises a mixture of acrylic acid and methacrylic acid, the weight ratio of acrylic acid to methacrylic acid is at least 0.8:1, in one embodiment at least 1:1, in one embodiment at least 1.2:1, in one embodiment at least 1.4:1, in one embodiment at least 1.6:1, in one embodiment at least 1.8:1, in one embodiment at least 2.0:1, at least in one embodiment 2.2:1, in one embodiment at least 2.4:1, in one embodiment at least 2.5:1. In one embodiment component (b) is 100% acrylic acid.

Component (c)
In order to modify or enhance certain properties of the polymer, for example, adherence to the hair, water-solubility, hardness, flexibility, antistatic properties, and the like, the polymers of the invention comprise two or more copolymerizable monomers of component (c). Without wishing to be bound by theory, it is believed that the use of two or more different monomers in component (c) introduces more complexity and more disruptions into the polymer structure, and makes the polymer less crystallizable, thereby unexpectedly improving certain properties that make the polymer suitable for use in a hair fixative formulation.

In one embodiment of the film forming copolymer, component (c) is two or more copolymerizable comonomers selected from the group consisting of ($C_1$-$C_{12}$)alkyl (meth) acrylates. Among the copolymerizable monomers of component (c) are the acrylic and methacrylic acid esters of aliphatic alcohols having from 1 to 12 carbon atoms such as methyl, ethyl, propyl, butyl, octyl and lauryl alcohols.

In one embodiment of the film forming copolymer, at least one of said two or more copolymerizable comonomers of component (c) is a ($C_1$-$C_2$)alkyl(meth)acrylate.

In one embodiment of the film forming copolymer, one of said two or more copolymerizable comonomers of component (c) is a ($C_1$-$C_2$)alkyl(meth)acrylate and one of said two or more copolymerizable comonomers of component (c) is a ($C_2$-$C_4$) alkyl(meth)acrylate that is different from the first ($C_1$-$C_2$)alkyl (meth)acrylate. In one embodiment the alkyl group of the ($C_2$-$C_4$)alkyl(meth)acrylate is branched.

In one embodiment of the film forming copolymer, one of said two or more copolymerizable comonomer of component (c) is methylmethacrylate and one of said two or more copolymerizable comonomers of component (c) is isobutylmethacrylate. In one embodiment the weight ratio of isobutylmethacrylate to methylmethacrylate is 1:1, in one embodiment less than 1:1, in one embodiment less than 1:1.5, in one embodiment less than 1:2.0, in one embodiment less than 1:2.5, in one embodiment less than 1:3.

Component (d) (Optional)

In one embodiment the polymers of the present invention further comprise as component (d) one or more cationic monomers selected from a ($C_1$-$C_6$)alkylamino ($C_2$-$C_4$)alkyl (meth)acrylate, or a ($C_1$-$C_6$)alkylamino($C_2$-$C_4$)alkyl(meth)acrylamide. The amino group of the monomer of component (d) can be mono-substituted or di-substituted with alkyl. In one embodiment component (d) comprises tertiary-butyl aminoethyl methacrylate. In one embodiment component (d) comprises dimethylaminopropyl methacrylamide.

The Copolymer

In order to provide a film forming polymer that will function effectively in a hair fixative composition to provide good compatibility with solvents and propellants, good removability, and good aesthetic and holding properties, it has been found that it is necessary to achieve a balance of properties by careful selection of the comonomers of each of the components and by corresponding adjustments of the proportions of each of the components in the film-forming copolymer. Such careful selection of the comonomers and their relative proportions also surprisingly allows the preparation of effective film-forming copolymers that use proportionately less of the more expensive monomers than prior art polymers, and in some embodiments can allow the complete avoidance of certain more expensive comonomers. For example, when the relative proportion of component (a) is reduced relative to prior art polymers, then the relative proportion of component (b) can be reduced and the relative proportion of component (c) increased to achieve the desired compatibility of the copolymer in certain solvent and propellant systems.

In order to provide polymers which will function particularly efficiently in the novel hair fixing compositions of this invention, the copolymer will contain 10-30% of the comonomers of component (a), 14-21% of the comonomers of component (b), and 40-76% of the two or more comonomers of component (c); these percentages being based on the total weight of the copolymer.

In one embodiment the polymers of the invention contain 10-30%, in one embodiment 10% to less than 30%, in one embodiment 15% to 29% or less, in one embodiment 15% to 28% or less, in one embodiment 15% to 26% or less, in one embodiment 15% to 24% or less, in one embodiment 15% to 22% or less, in one embodiment 15% to 20% or less, of the N-alkyl (meth)acrylamide of component (a).

In one embodiment the polymers of the invention contain 14-21%, in one embodiment 16-21%, in one embodiment 18-21%, in one embodiment 19-21%, and in one embodiment 20-21%, of the at least one acidic comonomer of component (b).

In one embodiment the polymers of the invention contain 40-76%, in one embodiment 45-70%, in one embodiment 45-65%%, in one embodiment 45-60%, of the combined at least two copolymerizable comonomers of component (c).

In one embodiment, the copolymer contains 0.1-5% of the optional component (d), in one embodiment 0.1-4%, in one embodiment 0.1-3%, in one embodiment 0.1-2%, in one embodiment 0.1-1%, in one embodiment 0.1-0.5%.

In one embodiment the present invention comprises a hair fixative composition comprising a film forming polymer that is prepared from monomers comprising (a) 10-30% by weight of one or more copolymerizable comonomers selected from the group consisting of N-alkyl(meth)acrylamide wherein the alkyl group thereof contains from 2 to 12 carbon atoms, wherein for at least one of said copolymerizable comonomers the alkyl group contains from 5 to 12 carbon atoms;

(b) 14-21% by weight of one or more acidic copolymerizable comonomers selected from the group of acrylic acid and optionally one or more from the group of methacrylic acid, crotonic acid, itaconic acid, maleic acid, fumaric acid, and the ($C_1$-$C_4$) alkyl half esters of maleic and fumaric acids; and (c) 40-76% by weight of two or more copolymerizable comonomers selected from the group consisting of ($C_1$-$C_{12}$) alkyl (meth)acrylates, wherein at least one of said two or more copolymerizable comonomers is a ($C_1$-$C_2$)alkyl (meth)acrylate.

In one embodiment the present invention comprises a hair fixative composition comprising a film forming polymer that is prepared from monomers comprising (a) 25-30% by weight N-tertoctyl acrylamide, (b) at least 19% by weight acrylic acid or a combination of acrylic acid and methacrylic acid, (c) at least 40% by weight combined methylmethacrylate and $C_4$ alkylacrylate, and (d) less than 1% by weight of a ($C_1$-$C_6$)alkyl ($C_2$-$C_4$)aminoalkyl(meth)acrylate.

A preferred film-forming polymer of the present invention (preferred because of its combination of excellent properties of curl retention, adherence to the hair, clarity, gloss, compatibility with solvents and propellants, shampoo removability, aesthetic properties such as beading gloss, stiffness, spring and webbing, and the like) will contain 15-30% of N-tert-octyl acrylamide as component (a), 14-21% of combined of acrylic acid and optional methacrylic acid as component (b), 45-60% of combined isobutyl methacrylate and methyl methacrylate as component (c), and less than 1% of tertiary-butyl aminoethyl methacrylate as optional component (d). In one embodiment the preferred film-forming copolymer contains no hydroxyalkyl (meth)acrylate.

As for the actual preparation of these film forming polymers, there may be employed any of the usual vinyl polymerization methods which are well known to those skilled in the art and which are particularly suited for the polymer whose preparation is desired. Thus, the polymers may be prepared by means of free radical initiated processes utilizing bulk, suspension, solution, or emulsion polymerization techniques. The polymers may, if desired, be converted into relatively large particles known as beads or pearls by dispersing the solution polymerized polymer in water and thereafter driving off the solvent followed by separating and drying the particles.

Variations on the general copolymerization techniques described above and in the art are encompassed within the invention. For example, the relative ratios of the monomers in both the initial reactor charge and in subsequent additions to the polymerization reactor can be selected to take into account differences in reactivities between the reacting species. The rates of addition of the comonomers to the reactor also can be selected to account for such different reactivities. There could also be some variations in grades of monomers being used. It is also possible to affect polymer molecular weight by varying the levels of solvent and/or initiator, and/or by using a chain transfer agent. It is also possible to use reclaimed grades of the solvent for economic purposes. Such variations of the copolymerization process will be readily understood by those skilled in the art.

Neutralization

The acidic comonomers of component (b) make it possible for the resultant copolymer to be neutralized by reaction with an appropriate base in order that it may ultimately exhibit the requisite water solubility. These acidic comonomers may be neutralized prior to the copolymer being incorporated into the ultimate hair fixing formulation thus permitting these formulations to be removed from the hair merely by rinsing with water. However, if such copolymers are not pre-neutralized in this manner, removal may still be readily effected by the application of an alkaline aqueous solution, for example, soap and water. It should be noted that for purposes of this invention the term water solubility is meant to include both water solubility in its usual meaning as well as water dispersibility wherein the resulting films are sufficiently hydrated and softened by contact with water so as to be easily removed from the hair by the application of water and either soap or shampoo.

The acrylic polymer resins can be completely or partially neutralized in a solvent system. When the acrylic polymers are to be used in high VOC aerosol hair fixative formulations then the neutralization can be carried out in an organic solvent such as ethanol. When the acrylic polymers are to be used in low VOC non-aerosol formulations then the neutralization can be carried out in a solvent system wherein water is the primary solvent, such that a homogeneous solution of the partially-neutralized acrylic polymer in the solvent system is formed. The statement that water is the primary solvent means that water is always the major constituent of the solvent system. That is to say, the solvent system always contains greater than 50 weight percent of the water, preferably greater than 60 weight percent of the water and even more preferably greater than 75 weight percent of the water, based on the total weight of the solvent system. The solvent system may further include organic solvents such as ethanol, isopropanol, acetone, ethylene glycol dimethyl ether (EGDME) and methyl ethyl ketone.

In one embodiment of a process for preparing the homogeneous solution of the partially-neutralized acrylic polymer, a two-step process may be utilized wherein the acrylic polymer first is neutralized in the solvent system with a neutralizing base to form a homogeneous solution of the neutralized acrylic polymer and then acid is added to the solution of the neutralized acrylic polymer under conditions effective to form a homogeneous solution of the partially-neutralized acrylic polymer in the solvent system. Neutralized acrylic polymer, as used herein, is used to denote the acrylic polymer after it has been neutralized with the neutralizing base, but before the acid is added to the solution of the neutralized acrylic polymer. Partially-neutralized acrylic polymer, as used herein, is used to denote the acrylic polymer after both the neutralization with base and the addition of acid has been completed.

In certain embodiments, the acrylic polymer, typically in powder form, is combined with the solvent system and an amount of the neutralizing base which is effective to neutralize the acrylic polymer to the extent that the neutralized acrylic polymer is soluble in the solvent system, thereby forming a homogeneous solution of the neutralized acrylic polymer in the solvent system. Preferably, the neutralizing base is added to the solvent system in predetermined effective amounts. The acrylic polymer is then added to the mixture of the solvent system and the neutralizing agent with stirring until the homogeneous solution of the neutralized acrylic polymer is formed. Dissolution of the neutralized acrylic polymer in the solvent system preferably is completed without the necessity of inputting energy into the system, such as high shear mixing or heating. Applicable neutralizing bases include, without limitation, sodium and potassium hydroxide, ammonia, primary, secondary and tertiary amines, alkanolamines and hydroxyamines, such as 2-amino-2-methyl-propanol and 2-amino-2-methyl-1,3-propanediol, respectively. The effective amount of the neutralizing base which is utilized will depend on the particular level and type of acidic monomer used to prepare the acrylic polymer. The effective amount of neutralizing base may be a molar ratio of base to the carboxyl groups contained in the acrylic polymer which is greater than or equal to 0.9:1, preferably, from about 0.9:1 to about 2:1, and more preferably from about 0.9:1 to about 1.5:1. The solution of the neutralized acrylic polymer must be homogeneous and must be stable from phase separation and precipitation. The pH of the solution of the neutralized acrylic polymer generally will be about 7 or greater, but typically less than 10. In one embodiment of the invention the polymer is 90-100% neutralized, and the pH of the solution of the polymer is in the range of 8-9.

In the systems where water is the primary solvent, after the homogeneous solution of the neutralized acrylic polymer is prepared a water-soluble acid is added to the solution of neutralized acrylic polymer to reduce the level of neutralization of the neutralized acrylic polymer, thereby forming a partially-neutralized acrylic polymer. The acid is added in an amount and under conditions which are effective to provide a homogeneous solution of the partially-neutralized acrylic polymer in the solvent system. Water-soluble acids which may be used include both organic and inorganic acids. Exemplary acids include, without limitation, acetic acid, nitric acid, phosphoric acid, sulfuric acid, hydrochloric acid, butyric acid and propionic acid. The effective amount of acid will depend on factors such as the specific acidic monomer used, the level at which the acid monomer is used, the concentration of the solution of the neutralized polymer and the relative strength of the acid. Where the effective amount of neutralizing base may be a molar ratio of base to the carboxyl groups contained in the acrylic polymer which is greater than or equal to 0.9:1, then the effective amount of acid is a molar ratio of acid to the carboxyl groups contained in the acrylic polymer greater than or equal to 0.1:1, preferably from about 0.9:1 to about 2:1, more preferably from about 1:1 to about 1.5:1 and even more preferably from about 0.2:1 to about 0.8:1. The solution of the partially-neutralized acrylic polymer must be homogeneous and must be stable from phase separation and precipitation, and most preferably forms clear, continuous films which are redispersible in water, i.e., readily removable from hair with water and/or shampoo.

The acid is added to the solution of the neutralized acrylic polymer under conditions effective to provide the homogeneous solution of the partially-neutralized acrylic polymer. In certain embodiments, the acid should be diluted in water to a concentration effective to provide the homogeneous solution of the partially-neutralized acrylic polymer prior to the addition thereof to the solution of the neutralized acrylic polymer. Furthermore, the acid should be added over a period of time which is effective to provide the homogeneous solution of the partially-neutralized acrylic polymer. The concentration of the acid and the time period over which the acid is added will depend on factors such as the concentration of the neutralized acrylic polymer and the relative strength of the acid, for example. If either the concentration of the acid is too high or the acid, diluted or undiluted, is added too quickly, precipitation of the polymer will occur. While slight precipitation may be remedied by additional mixing, higher levels of precipitation or formation of larger polymer particles caused by improper acid addition may not be rectified, regardless of further mixing. As with the homogeneous solution of the neutralized acrylic polymer, dissolution of the partially-neutralized acrylic polymer in the solvent system preferably is completed without the necessity of inputting energy into the system, such as high shear mixing or heat. One skilled in the art, having the benefit of the disclosure herein, will be able to ascertain readily what conditions of concentration and time of acid addition would be required in order to provide the homogeneous solution of the partially-neutralized acrylic polymer.

The pH of the solution of the partially-neutralized acrylic polymer will be sufficient for use in hair fixative composition. Preferably, the pH of the solution of the partially-neutralized acrylic polymer according to the present invention will range from about 5.5 to about 8.5, more preferably from about 6 to about 8, and most preferably is about 7. The homogenous solution of the partially-neutralized acrylic polymer will contain from about 1 to about 20 weight percent of the partially-neutralized acrylic polymer, preferably from about 2 to about 15 weight percent of the partially-neutralized acrylic polymer, based on the total weight of the solvent system and the partially-neutralized acrylic polymer.

The viscosity of the solution of the partially-neutralized acrylic polymer also will be suitable for use in hair fixative compositions. As is known in the art, solution viscosity is an important property of aerosol hair fixatives, where the balancing of aerosol spray characteristics (affected by solution viscosity) versus on-hair performance of the hair fixative (affected by the presence of water) presents a problem in low VOC hair fixatives. The viscosity of a 5 percent polymer solids solution of the partially-neutralized acrylic polymer in a solvent system consisting of water and EGDME at relative weight percent of 67/33 and at 25° C. preferably will range from about 2 to about 10 cp, more preferably from about 2 to about 7 cp.

In preparing the hair fixative compositions according to the present invention, the homogeneous solution of the partially-neutralized acrylic polymer is combined with additional water and optionally a propellant or emulsifier, thereby forming the hair fixative composition. Methods of combining the ingredients are well within the knowledge of one skilled in the art of preparing hair fixative compositions.

The acrylic hair fixative composition so prepared will comprise an amount of the partially-neutralized acrylic polymer which is effective to provide the hair fixative composition with sufficient hair fixative properties, preferably from about 3 to about 10 dry weight percent based on the total weight of the hair fixative composition.

The acrylic polymer resins can be partially or fully neutralized in a solvent system wherein an organic solvent is the primary solvent, such that a homogeneous solution of the partially or fully neutralized acrylic polymer in the solvent system is formed. The solvent system generally comprises solvents such as ethanol, isopropanol, acetone, ethylene glycol dimethyl ether (EGDME) and methyl ethyl ketone. In such systems, an optional amount of water can be added as a secondary solvent. The amount of water will generally be contained from 5 to 15% of the formulation.

The Hair Fixative Formulations

The selection of the solvent(s) and propellant(s) in a hair fixative formulation can be based on different factors such as geographical preferences, availability and regulations concerning the components, compatibility with other ingredients, and type of hold that is ultimately desired. As discussed above, it is also possible to alter the characteristics of the polymer to optimize its utilization in a specific type of chassis (i.e., combination of solvent system and propellant). For example, aqueous-based systems might rely on lower molecular weight polymers to allow for an aesthetically pleasing spray delivery. Similarly, the ability of the polymer to flow and provide good binding to hair can be altered by varying its composition and/or molecular weight. While too low molecular weight polymers might not provide sufficient hold, too high molecular weight polymers might not deliver the right characteristics of delivery and flow, and hence might impart reduced benefits.

The hair fixative compositions may be in the form of an aerosol or non-aerosol spray, a mousse, gel, wax, pomade or a hair-setting lotion. The compositions may contain up to 40 weight percent, in some embodiments up to 35 weight percent, of propellants. Various types of aerosol propellants are well known to those skilled in the art. Typical propellants include ethers, compressed gases, halogenated hydrocarbons and hydrocarbons. Exemplary propellants are dimethyl ether, compressed nitrogen, air or carbon dioxide, propane, isobutane, heptane, trichlorofluoromethane, dichlorodifluoromethane, and 1,1-difluoroethane such as Dymel® 152a (available from DuPont), as well as mixtures of the latter propellants. These propellants are readily compatible with the polymer-solvent solutions utilized in this invention. The hair fixative compositions may further include other materials or additives such as fragrances, preservatives, colorants, plasticizers, emulsifiers, conditioners, neutralizers, glossifiers and the like. Such propellants, organic solvents and materials or additives are commonly used in hair fixative compositions known heretofore.

Mousses according to the present invention further comprise from about 0.25 to 6 weight percent, preferably 0.25 to 3 weight percent, of an emulsifier. The emulsifier may be nonionic, cationic, anionic or amphoteric. Exemplary nonionic emulsifiers include Tergitol® NP 15 (INCI designation—Nonoxynol 15) and Brij 97 (INCI designation—Oleth 10). The mousses also comprise from about 2.5 to 25 weight percent, preferably 5 to 15 weight percent, of a propellant as discussed above. The mousses may comprise additional ingredients as discussed above, with the balance of the mousse comprising water. Optional additives may be incorporated into the hair fixative compositions of the present invention in order to modify certain properties thereof. Among these additives may be included plasticizers such as glycols, phthalate esters and glycerine; silicones; emollients, lubricants and penetrants such as lanolin compounds, protein hydrolyzates and other protein derivatives, ethylene oxide adducts, and polyoxyethylene cholesterol; U.V. absorbers; dyes and other colorants; and perfumes.

The resulting hair fixative compositions of the present invention exhibit all of the characteristics required of a hair fixative. Their films are transparent, glossy, and continuous. They possess good antistatic properties, are readily removed by soapy water or shampoos, allow the hair to be readily recombed, have excellent curl retention under high humidity conditions, and other desirable properties as illustrated in the Examples below.

In general, the method for preparing hair spray formulations of this invention merely involves dissolving or diluting the polymer in the selected solvents, adding any modifying agents whose presence may be desired, and thereupon combining the resulting solution with the selected aerosol propellant.

Thus, it may be noted that the novel aerosol hair spray formulations of this invention will in all cases contain at least three essential components. The first of the latter components will be what may be termed as the active ingredient comprising one or more of the above described polymers which serves as the film former for the formulation. Secondly, there will be one or more solvents which serve as vehicles for the polymer. And, finally, there is the propellant which serves to affect the discharge of the aforedescribed polymer and vehicle from the container wherein the formulation is packaged. Water is not ordinarily present as the primary solvent in aerosol formulations, but may be included in some formulations.

With regard to proportions, the final hair spray formulations typically contain the polymer of the invention in a concentration ranging from about 0.25 to 7%, by weight; the solvent in a concentration ranging from about 8 to 90%, by weight; and the propellant in a concentration ranging from 10 to 45% by weight. The latter proportions should, however, be considered as being merely illustrative inasmuch as it may well be possible to prepare operable formulations having concentrations of components which fall outside the above suggested ranges.

In addition, it should be noted that the unique film forming polymers of this invention are equally effective when utilized in hair setting lotions, which usually consist of a solution (or dispersion) of the polymer in a suitable organic solvent, such as alcohol, together with water. Such lotions may be directly applied to the hair or they may be sprayed thereon utilizing conventional spray nozzles. The application of such lotions may take place prior to, during, or after the desired hair style has been achieved.

The latter hair lotions are prepared by merely admixing the film forming polymer with the selected solvent, such solvents usually comprising a mixture, with water or an alcohol such as ethanol or isopropanol. With regard to proportions, the lotions typically contain from about 0.5 to 7% by weight of the polymers of the invention while any desired ratio of alcohol to water in the solvent system may be utilized therein. An all alcohol system may also be used in some cases.

Optional additives may be incorporated into the hair fixing formulations of this invention in order to modify certain properties thereof. Among these additives may be included: plasticizers such as glycols, phthalate esters and glycerine; silicones; emollients, lubricants and penetrants such as lanolin compounds, protein hydrolyzates and other protein derivatives, ethylene oxide adducts, and polyoxyethylene cholesterol; U.V. absorbers; dyes and other colorants; and, perfumes. As previously noted, the polymers of this invention show little or no tendency to chemically interact with such additives.

The invention further includes a process for fixing hair comprising applying to the hair an effective amount of a hair fixative composition as disclosed herein. For example, where the composition is in the form of a mousse, gel or hairsetting lotion the fixative composition can be applied prior to or during styling; and where the composition is in the form of an aerosol hairspray the fixative composition can be applied after hairstyling to hold the style.

In the following examples, which further illustrate embodiments of this invention, all parts given are by weight unless otherwise indicated. The following examples are not intended to and should not be construed to limit the scope of the invention, the scope of which is limited only by the claims appended hereto.

Examples

The following examples are offered to further illustrate the invention and are not meant to limit the scope of the invention in any way.

Example 1—Polymer Preparation

The following example illustrates a representative method for the polymerization of typical polymers suitable for use in the compositions of the present invention.

A reaction vessel fitted with a condenser and means for mechanical agitation was charged with 0.6 g of dibenzoyl peroxide, 10.15 grams of ethanol, 37.15 grams of isopropyl acetate, and 18% of a monomer mixture containing 55.8 grams of t-octyl acrylamide ("t-OA"), 23.3 g of acrylic acid ("AA"), 14.0 g of methacrylic acid ("MAA"), 46.5 g of isobutyl methacrylate ("iBMA"), and 46.5 g of methyl methacrylate ("MMA"). The system was heated to reflux temperature and after 15 minutes the remainder of the monomer mixture was added over 4 hours. After 2 hours was also started the addition of 0.3 g of dibenzoyl peroxide in 37.39 g of ethanol over 2 hours. At the end of the monomer addition, a mixture of 0.39 g of dibenzoyl peroxide in 23.32 g of isopropyl acetate and 19.2 g of ethanol was added over 3 hours. The system was further held at reflux for an additional 4 hours 15 minutes. The polymer was then recovered and dried as Polymer Sample 1 in Table 1 below.

Other polymer samples made in accordance with this polymerization procedure include the polymer samples listed in Table 1, in which the values are the weight percent of each monomer in the polymer. Where tertiary-butyl aminoethyl methacrylate ("t-BAEMA") was used it was added at the same time as the other monomers.

TABLE 1

| Polymer Sample No. | t-OA | AA | MAA | iBMA | MMA | t-BAEMA |
|---|---|---|---|---|---|---|
| 1 | 30 | 12.5 | 7.5 | 25 | 25 | 0 |
| 2 | 30 | 12.5 | 7.5 | 25 | 25 | 0 |
| 3 | 30 | 12.5 | 7.5 | 24.75 | 24.75 | 0.5 |
| 4 | 10 | 5 | 15 | 24.75 | 44.75 | 0.5 |
| 5 | 30 | 20 | 0 | 15 | 34.5 | 0.5 |
| 6 | 30 | 12.5 | 7.5 | 24.95 | 24.95 | 0.1 |
| 7 | 30 | 12.5 | 7.5 | 24.95 | 24.95 | 0.1 |
| 8 | 20 | 5 | 15 | 15 | 44.9 | 0.1 |
| 9 | 15 | 5 | 10 | 25 | 44.9 | 0.1 |
| 10 | 24 | 12 | 8 | 17 | 38.9 | 0.1 |
| 11 | 20 | 9 | 11 | 20 | 39.9 | 0.1 |
| 12 | 26 | 14 | 6 | 15 | 38.9 | 0.1 |
| 13 | 26 | 14 | 6 | 15 | 38.9 | 0.1 |
| 14 | 26 | 13.5 | 6.6 | 26.9 | 26.9 | 0.1 |
| 15 | 26 | 14.5 | 6.1 | 26.65 | 26.65 | 0.1 |
| 16 | 26 | 13.5 | 5.2 | 27.6 | 27.6 | 0.1 |
| 17 | 26 | 14.5 | 4.7 | 27.35 | 27.35 | 0.1 |
| 18 | 26 | 14 | 6.7 | 26.6 | 26.6 | 0.1 |
| 19 | 26 | 14 | 6 | 26.95 | 26.95 | 0.1 |
| 20 | 26 | 14 | 5.3 | 27.3 | 27.3 | 0.1 |
| 21 | 26 | 13.5 | 7.3 | 26.55 | 26.55 | 0.1 |
| 22 | 26 | 13.5 | 6.6 | 26.9 | 26.9 | 0.1 |

TABLE 1-continued

| Polymer Sample No. | t-OA | AA | MAA | iBMA | MMA | t-BAEMA |
|---|---|---|---|---|---|---|
| 23 | 26 | 13.5 | 5.9 | 27.25 | 27.25 | 0.1 |
| 24 | 26 | 13.5 | 5.2 | 27.6 | 27.6 | 0.1 |
| 25 | 26 | 14 | 6 | 15 | 38.9 | 0.1 |
| 26 | 26 | 20 | 0 | 15 | 38.9 | 0.1 |
| 27 | 26 | 20 | 0 | 15 | 38.9 | 0.1 |
| 28 | 26 | 20 | 0 | 15 | 38.9 | 0.1 |
| 29 | 26 | 19 | 0 | 15.5 | 39.4 | 0.1 |
| 30 | 26 | 21 | 0 | 14.5 | 38.4 | 0.1 |
| 31 | 26 | 14.5 | 6.1 | 14.7 | 38.6 | 0.1 |
| 32 | 26 | 13.5 | 7.3 | 14.5 | 38.5 | 0.1 |
| 33 | 26 | 14.5 | 4.7 | 15.4 | 39.3 | 0.1 |
| 34 | 26 | 13.5 | 5.3 | 15.6 | 39.5 | 0.1 |
| 35 | 22 | 20 | 0 | 17 | 40.9 | 0.1 |
| 36 | 29 | 20 | 0 | 13.5 | 37.4 | 0.1 |
| 37 | 22 | 14 | 6 | 17 | 40.9 | 0.1 |
| 38 | 29 | 14 | 6 | 13.5 | 37.4 | 0.1 |
| 39 | 23.98 | 20.98 | 0.00 | 24.40 | 30.54 | 0.10 |
| 40 | 29.97 | 9.64 | 9.91 | 34.61 | 15.78 | 0.10 |
| 41 | 27.54 | 9.62 | 5.36 | 21.0 | 36.38 | 0.10 |

Example 2—Preparation of Polymer-Solvent-Propellant Formulations

Selected polymer samples were neutralized in ethanol solvent and blended with propellant according to the following procedure to provide formulations for further evaluations:

Formulation Preparation Procedure:
1. To the main mixing vessel charge all the ethanol contained in the formulation.
2. Begin mixing with propeller agitation (Adjust the speed of the speed of the mixing until there is a vortex pulled ⅔ of the way down the mixing shaft).
3. Add the Aminomethylpropanol (neutralizing agent).
4. Slowly add the polymer powder by sifting it into the side of the vortex. Allow the polymer to disperse completely.
5. Maintain mixing until the polymer is completely dissolved and the solution is clear.
6. Add propellant. In the following samples the propellant is heptane at 40% of the total formulation, unless indicated otherwise.

In each sample formulation reported herein, unless stated otherwise the formulation was 3 wt % polymer, ethanol QS to 60 wt %, sufficient neutralization agent to achieve 100% neutralization, and 40 wt % propellant.

Example 3—Turbidity

Samples of formulations containing polymer samples 2-5 were tested in order to determine the turbidity of the sample formulations. The neutralized polymer/solvent concentrates (no propellant present) were placed in a HACH tube (glass tubes designed for the specific instrument). The samples were then measured on a HACH Turbidimeter (model number 2100N) and reported in NTU. Turbidity was measured at room temperature (approximately 23° C.). The results are reported in Table 2.

Example 4—Hair Swatch Sample Preparation for Subjective Evaluations

For the evaluations of beading, loss, stiffness, spring, webbing, dry feel, flake, dry comb, and anti-static, test swatches were prepared from 10" long×4.5 gram swatches of European virgin brown hair. Each swatch was sprayed on both sides from a distance of 6 inches with the sample formulation to be evaluated; specifically, each swatch was sprayed on one side a first time from root to tip for one second, and then from tip to root for one second. Then the swatch was turned over and the process was repeated. The samples were allowed to dry for one hour at 23° C. prior to the evaluation.

For the evaluations of shampoo removability, test swatches were prepared from 10" long×2 gram swatches of European virgin brown hair. Each swatch was sprayed from a distance of six inches with the sample to be evaluated by the same procedure described above, and allowed to dry for one hour at 23° C. The following additional steps were then followed:
1) Wet hair swatch with warm tap water, gently remove excess water and apply three (3) drops of shampoo along the length of the swatch.
2) "Work" shampoo into hair swatch and lather for 30 seconds.
3) Rinse hair swatch under running warm tap water for 30 seconds.
4) Gently remove excess water, place on tray, and dry for one hour at 120° F.
5) Arrange swatches in four pairs ("test" formulation and "control" formulation)
    and present to panelist for evaluation, in each of the following areas in the exact order of Stiffness, Flake and Feel, as described below.

The shampoo used was 40.00 parts sodium laureth sulfate (Rhone-Poulenc), 27.59 parts by weight sodium lauryl sulfate (Henkel Corporation), 0.50 parts by weight cocamide DEA (Mona Industries, Inc.), 0.10 parts by weight Methylchloroisothiazolinone (and) Methylisothiazolinone (Rohm and Haas Company, Inc.), and 31.81 parts by weight deionized water; the shampoo composition was adjusted to pH 6.5-6.7 with 50% citric acid

Example 5—Evaluation of Shampoo Removability; and Subjective Tests

To evaluate the subjective properties, four panelists were used for each test. Each panelist was presented with two sample sets, for a total of eight sample sets per test. Each set included two samples; one swatch in each set was a control sample treated with a hair spray composition comprising the prior art AMPHOMER® polymer available from Akzo Nobel Surface Chemistry, LLC, and the other swatch in each set was a test sample treated with a hair spray composition comprising a novel polymer as identified herein. "Blind" evaluations are performed on the "test swatch" (treated with experimental product) and the "control swatch" (for a total of eight sets of comparisons). In each set the control hair spray formulation and the test hair spray formulation comprised the same solvent and propellant. Thus for each test criterion eight sets of samples were evaluated in a "blind" comparison of samples with each novel polymer against the control samples. In each performance area, the panelist must select one swatch as better than the other for the types of attributes that are indicated.

Subjective Properties Description:
Beading:
Visually examine the swatch for dried polymer beads. Choose the swatch which has more beading.

Gloss:

Gently handle the swatches so as not to break the films. Visually inspect the swatches to determine which has more shine/gloss.

Stiffness:

Gently handle swatches and feel for differences in stiffness. Using two fingers, hold the middle of the swatch in a horizontal position—does one bend more than the other?

Choose the one that is more rigid.

Spring:

While holding the swatch in one hand, gently pull on an edge with the other hand three times only. Look for spring back, and bounce. The more elastic the better the Spring.

Webbing:

While holding the swatch in both hands, gently pull outward on the edges approx. 4". (Do this three times only to avoid damage to the bonds. If the bonds are destroyed then the dry combing may appear to be easier to comb). The more net like the better the Webbing.

Flake: Visually inspect both swatches. Holding the swatches at the bound end, run your fingernail down the length of the tress, then inspect. Choose the one with more flake.

Dry Feel:

Handle swatches and determine preference. Choose the one that feels more silky/cleaner.

Anti-Static:

Holding swatch at bound end comb through vigorously 10 times then evaluate for extent of fly aways generated. Choose the one with more fly aways.

Dry Comb:

Comb through each swatch (5) times and evaluate ease of combing. Choose the one that combs more easily.

0/8-1/8: Statistically inferior 2/8-6/8: Statistically not different

7/8-8/8: Statistically superior

Selected polymers listed in Table 2 were evaluated for compatibility in heptane which is representative of a hydrocarbon type propellant. Thus in Table 2 below a "+" sign indicates that the tested sample was preferred over the control for at least 7 of 8 test sets, a "−" sign indicates that the control was preferred over the test sample for at least 7 of 8 test sets, an "=" sign indicates that there was not a statistical difference between the sample and the control, and a blank space indicates that the evaluation was not performed.

TABLE 2

| Polymer Sample No. | Turbidity, ntu; 40% heptane | Shampoo removability | Beading | Gloss | Stiffness | Spring | Webbing |
|---|---|---|---|---|---|---|---|
| 2 | 1.63-3.22 | = | = | = | + | + | + |
| 3 | 3.25-8.29 | − | = | = | + | = | = |
| 4 | Prec. | | | | | | |
| 5 | Prec. | | | | | | |
| 6 | | = | = | = | + | = | = |
| 7 | | − | = | + | + | + | = |
| 8 | | = | = | = | = | = | = |
| 9 | | − | | | | | |
| 10 | | − | = | = | = | = | = |
| 11 | | (poor compatibility) | | | | | |
| 12 | | = | − | = | = | = | = |
| 39 | = | = | = | = | = | = | = |
| 40 | = | = | = | = | = | = | = |
| 41 | = | = | = | = | = | = | = |

| Polymer Sample No. | Dry Comb | Flake | Anti-Stat | Feel |
|---|---|---|---|---|
| 2 | − | = | = | = |
| 7 | = | = | = | = |
| 12 | = | − | = | = |
| 39 | = | = | = | = |
| 40 | = | − | = | = |
| 41 | + | = | + | = |

Three properties that measure overall hold are stiffness, spring, and webbing. Stiffness is measured by a panelist choosing the swatch that is harder feeling or stiffer. Spring and webbing are a measure of the cohesive and adhesive properties of the polymer with the hair and the polymer. In subjective testing the panelists are asked to choose the swatch with more webbing and the swatch that springs back the fastest and closest to its original shape.

It can be noted from Table 2 that, unexpectedly, some polymers with a content of less than 30 parts of the tOA (t-octylacrylamide) monomer deliver hydrocarbon compatibility, shampoo removability, and superior performance to the control in subjective analysis. Example 7, for example, delivers superior gloss, stiffness, and spring, a measure of durability (natural feel) against the control.

Example 6—High Humidity Curl Retention

The curl retention properties of polymeric hair spray resins were measured on 6" long×3.75-4.0-gram swatches of European virgin brown hair (9 replicate swatches per sample) at 70° F./90% Relative Humidity over a period of 24 hours according to the following procedure.

1. Wet hair swatch, comb through to remove tangles and squeeze out excess water (run swatch between thumb and index finger).
2. Apply sample to swatch, gently "work into" swatch and comb through.
3. Roll swatch on ½" diameter Teflon mandrel. Carefully remove rolled swatch from mandrel and secure with two hair clips. While curling hair, make sure to keep the curl tight and continuous along the mandrel, with no gaps. Secure hair on mandrel with plastic Tygon (pre-cut) clips, one on each end of the curl. Make sure the curl is tight around the mandrel with no exposed stray hairs.
4. Place curls on tray and dry in 110° F. oven overnight.
5. Remove dried curls from oven and let cool for 30 minutes. Carefully remove clips and curl from mandrel.
6. Suspend curls, from bound end of swatch. Apply a controlled amount of hair spray to curl. When evaluating an aerosol hair spray, a two second burst is evenly applied to the front and back of each curl from a distance of 6". When spraying curls, spray five curls of the first product, then five curls of the second product, and so on for all the formulas being used. Then reverse the order, working backwards, until the final four of each set are complete.
7. Lay the freshly sprayed curls on a clean tray (foil-covered) and allow to air dry for one hour.
8. Suspend the dry curls on a Guide Board, taking care to touch only the bound end of each swatch.
9. Take initial curl length readings before placing boards and curls into environmental chamber (70° F., 90% relative humidity).
10. Record curl lengths at the 15, 30, 60, 90, 2, 3, 4, 5, and 24 hour time intervals.
11. Calculate % Curl Retention and comparison of samples.

Sample formulations were prepared with ethanol solvent and 40% heptane propellant.

Polymer samples 3, 6, 8, 12, 33 and 39-41 were all evaluated and found to have HHCR performance equal to that of the control prior art polymer AMPHOMER®.

Example 7—Evaluation of Formulations Prepared with Hydrofluorocarbon Propellant

The polymers listed in Table 3 were evaluated for compatibility in 1,1-difluoroethane which is representative of a hydrofluocarbon propellant.

The evaluations in Table 3 were conducted on mannequin heads instead of hair swatches, where one side was sprayed with the experimental product and the other with the prior art AMPHOMER® polymer control formulation. Each side was sprayed with 10 bursts of the formulation, and the evaluation was performed after drying of the head. As before, a subjective evaluation result showing a preference by 7 or 8 out of the 8 evaluations is indicative of a statistically significant difference.

TABLE 3

| Polymer Sample No. | Turbidity | Beading | Gloss | Stiffness | Spring | Webbing |
|---|---|---|---|---|---|---|
| 6 | clear | − | = | = | + | + |
| 7 | clear | = | + | + | + | + |
| 12 | clear | = | + | = | = | = |

Table 3 shows again a superior benefit to examples 6 and 7 in a different propellant system, a hydrofluorocarbon.

Example 8—Evaluation of Formulations Prepared with Hydrocarbon Propellant

The polymers listed in Table 4 were evaluated on hair swatches for compatibility in A46, a commercially available mixture of isobutane and propane, which is representative of a hydrocarbon propellant, except that samples 27b and 27c were run in different solvents as indicated. Examples 26 and 33 showed superior performance against the control. It might appear surprising that example 27, of the same composition as example 26, does not exhibit a superior performance against the control. It is believed that this difference is due to a difference in molecular weight: the weight average molecular weight for sample 27 is about 160,000, whereas it is lower at about 130,000 for sample 26. While not bound to theory, the flow properties of example 27 might not be as conducive for a suitable coverage of the hair, leading to a decreased performance in subjective attributes. It can also be noted that examples 26 and 33 have similar compositions, with a difference in the level and type of acidity (20 and 19.2 parts, respectively), whereas examples of similar compositions with higher levels of acidity, i.e., greater than 20%, do not show compatibility in a hydrocarbon type propellant.

TABLE 4

| | Beading | Gloss | Stiffness | Spring | webbing | Feel |
|---|---|---|---|---|---|---|
| 26 | = | = | + | + | + | = |
| 27 | = | = | = | = | = | = |
| 27b (DME) | = | = | = | = | = | − |
| 27c (152A + 10% H$_2$O) | = | = | = | = | = | = |
| 28 | = | = | = | = | = | = |
| 15 | = | = | = | = | = | = |
| 24 | + | = | = | = | = | = |
| 21 | = | = | = | = | = | − |
| 17 | + | = | = | = | = | = |
| 29 | − | = | = | = | = | = |
| 19 | = | = | = | = | = | = |
| 30 | = | = | − | = | = | = |
| 33 | = | + | = | + | + | = |
| 34 | = | = | = | = | = | = |
| 36 | = | = | = | = | = | = |
| 38 | = | = | = | = | = | + |

While a low amount of the t-octylacrylamide monomer tOA (e.g., about 22%) can lead to a poor compatibility in a hydrocarbon propellant, it has been discovered that this monomer can deliver superior performance when used at levels lower than 30%, as in examples 26 and 33.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described herein, the invention is not intended to be limited to the details shown. Rather, various modifications may be made in the details within the range and scope of equivalents of the claims and without departing from the spirit and scope of the invention.

What is claimed is:

1. A hair fixative composition comprising a film forming polymer that is prepared from:
   (a) 26% to 30% by weight of N-tert-octylacrylamide;
   (b) 12.5% to 20% by weight of acrylic acid and 0% to 7.5% by weight of methacrylic acid, wherein the film forming polymer is prepared from acrylic acid and methacrylic acid in a combined total of 19.2% to 20% by weight;
   (c) 15% to 25% by weight of isobutylmethacrylate and 24.5% to 39.3% by weight of methylmethacrylate, wherein the film forming polymer is prepared from isobutylmethacrylate and methylmethacrylate in a combined total of 49.9% to 54.7% by weight; and
(d) 0% to 0.1% by weight of tert-butylaminoethylmethacrylate.

2. The hair fixative composition of claim 1, wherein the film forming polymer is selected from the group consisting of film forming polymers A, B, C, D, E, and F comprising a copolymer of monomers according to the following table:

| Polymer | t-OA | AA | MAA | iBMA | MMA | t-BAEMA |
|---------|------|------|------|-------|-------|---------|
| A | 30 | 12.5 | 7.5 | 25 | 25 | 0 |
| B | 30 | 12.5 | 7.5 | 24.95 | 24.95 | 0.1 |
| C | 30 | 12.5 | 7.5 | 24.95 | 24.95 | 0.1 |
| D | 26 | 14 | 6 | 15 | 38.9 | 0.1 |
| E | 26 | 20 | 0 | 15 | 38.9 | 0.1 |
| F | 26 | 14.5 | 4.7 | 15.4 | 39.3 | 0.1 | wherein
t-OA represents N-tert-octylacrylamide;
AA represents acrylic acid;
MAA represents methacrylic acid;
iBMA represents isobutylmethacrylate;
MMA represents methylmethacrylate; and
tBAEMA represents tert-butylaminoethylmethacrylate; and
the numbers given in the table each represent percentages by weight, in each case based on a total weight of the film forming polymer.

3. The hair fixative composition of claim 2, wherein the film forming polymer is selected from the group consisting of film forming polymers D, E, and F comprising a copolymer of monomers according to the following table:

| Polymer | t-OA | AA | MAA | iBMA | MMA | t-BAEMA |
|---------|------|------|------|-------|-------|---------|
| D | 26 | 14 | 6 | 15 | 38.9 | 0.1 |
| E | 26 | 20 | 0 | 15 | 38.9 | 0.1 |
| F | 26 | 14.5 | 4.7 | 15.4 | 39.3 | 0.1 | wherein
t-OA represents N-tert-octylacrylamide;
AA represents acrylic acid;
MAA represents methacrylic acid;
iBMA represents isobutylmethacrylate;
MMA represents methylmethacrylate; and
tBAEMA represents tert-butylaminoethylmethacrylate; and
the numbers given in the table each represent percentages by weight, in each case based on a total weight of the film forming polymer.

4. The hair fixative composition of claim 1, wherein from 50 to 100% of the available carboxyl groups of the polymer are neutralized.

5. The hair fixative composition of claim 1 wherein the composition is in an aerosol spray and further comprises a solvent and an aerosol propellant therefor.

6. A process for fixing hair comprising applying to the hair the hair fixative composition of claim 1.

* * * * *